United States Patent

Bonutti et al.

[11] Patent Number: 5,601,590
[45] Date of Patent: Feb. 11, 1997

[54] EXPANDABLE CANNULAS

[75] Inventors: Peter M. Bonutti, Effingham; James S. Hawkins, Urbana, both of Ill.

[73] Assignee: General Surgical Innovations, Inc., Palo Alto, Calif.

[21] Appl. No.: 416,083

[22] Filed: Apr. 4, 1995

Related U.S. Application Data

[62] Division of Ser. No. 254,368, Jun. 6, 1994, which is a division of Ser. No. 13,942, Feb. 4, 1993, Pat. No. 5,320,611.

[51] Int. Cl.⁶ .................................................. A61M 29/02
[52] U.S. Cl. ........................................... 606/192; 600/207
[58] Field of Search ........................... 600/207; 606/192, 606/196, 193; 604/96

[56] References Cited

U.S. PATENT DOCUMENTS

| | | | |
|---|---|---|---|
| 577,775 | 2/1897 | Mussey | 606/192 |
| 1,735,519 | 11/1929 | Vance | 606/196 |
| 2,281,600 | 5/1942 | Ross | 606/192 |
| 4,299,227 | 11/1981 | Lincoff | 606/192 |
| 4,312,353 | 1/1982 | Shahbabian | 600/207 X |
| 4,465,072 | 8/1984 | Taheri | 606/192 X |
| 5,331,975 | 7/1994 | Bonutti | 606/192 X |
| 5,353,785 | 10/1994 | Wilk | 600/207 |
| 5,401,241 | 3/1995 | Delany | 604/43 |

FOREIGN PATENT DOCUMENTS

| | | | |
|---|---|---|---|
| 4012642 | 10/1991 | Germany | 606/192 |
| 969276 | 10/1982 | U.S.S.R. | 606/192 |

*Primary Examiner*—Michael H. Thaler
*Attorney, Agent, or Firm*—Lyon & Lyon

[57] ABSTRACT

Cannulas for surgical and medical use expand along their entire lengths. The cannulas are inserted through tissue when in an unexpanded condition and with a small diameter. The cannulas are then expanded radially outwardly to give a full-size instrument passage. Expansion of the cannulas occurs against the viscoelastic resistance of the surrounding tissue. The expandable cannulas do not require a full depth incision, or at most require only a needle-size entrance opening.

3 Claims, 2 Drawing Sheets

5,601,590

EXPANDABLE CANNULAS

RELATED APPLICATIONS

This application is a divisional of application Ser. No. 08/254,368, filed Jun. 6, 1994. The aforesaid application Ser. No. 08/254,368 is itself a divisional of application Ser. No. 08/013,942 filed Feb. 4, 1993 now U.S. Pat. No. 5,320,611. The benefit of the earlier filing dates of the aforementioned applications is claimed.

BACKGROUND OF THE INVENTION

The present invention relates to cannulas for surgical and medical use. A typical cannula is a fixed diameter tube which a surgeon uses to maintain an instrument passage through tissue to a subcutaneous working location. The surgeon must first make an incision the full depth of the cannula in order to insert the cannula. This traumatic action damages good tissue in order to get to bad tissue. It would be desirable to provide cannulas which do not require a full depth incision, or at least require only a needle-size entrance opening, and which still allow use of a cannula to maintain an instrument passage.

SUMMARY OF THE INVENTION

In accordance with the invention, cannulas are provided which expand along their entire lengths. The cannulas are inserted through tissue when in an unexpanded condition and with a small diameter. The cannulas are then expanded radially outwardly to give a full-size instrument passage. Expansion of the cannulas occurs against the viscoelastic resistance of the surrounding tissue. The expandable cannulas do not require a full depth incision, or at most require only a needle-size entrance opening.

BRIEF DESCRIPTION OF THE DRAWINGS

The foregoing and other features of the present invention will become apparent to one skilled in the art to which the present invention relates upon consideration of the following description of the invention with reference to the accompanying drawings, wherein.

DESCRIPTION OF PREFERRED EMBODIMENTS

Figure 1:
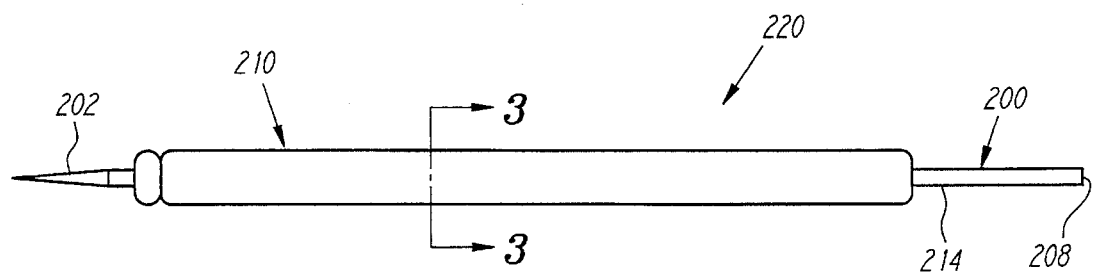
FIG. 1 is a side elevational view of a cannula in accordance with an embodiment of the present invention, shown in an unexpanded condition.
Figure 2:
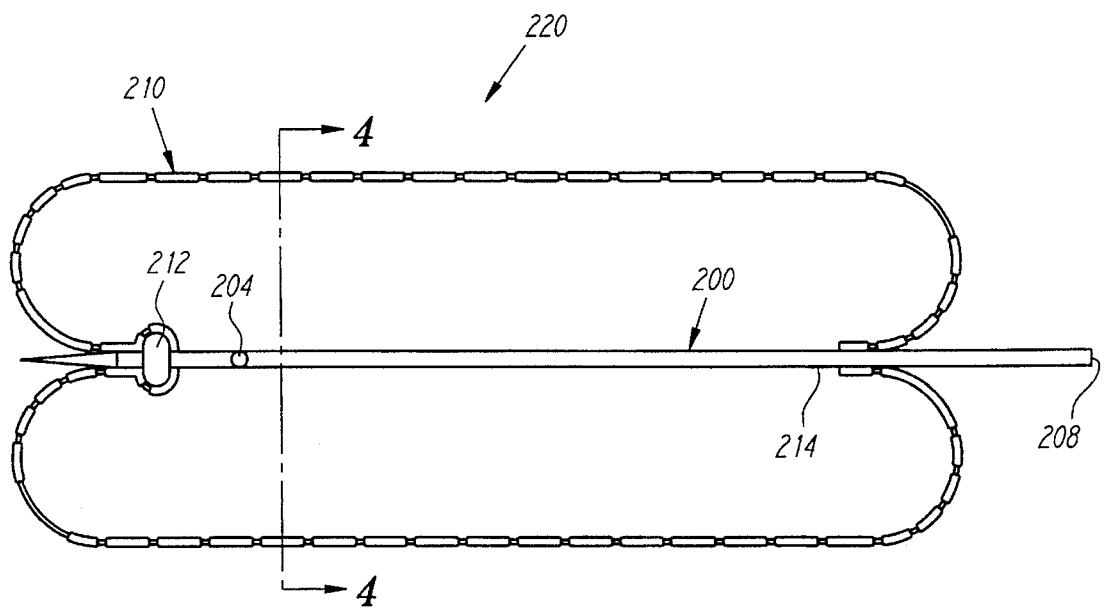
FIG. 2 is a longitudinal sectional view of the cannula of FIG. 1 in an expanded condition.
Figure 3:
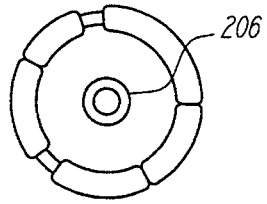
FIG. 3 is a sectional view taken along line 3—3 of FIG. 1.
Figure 4:
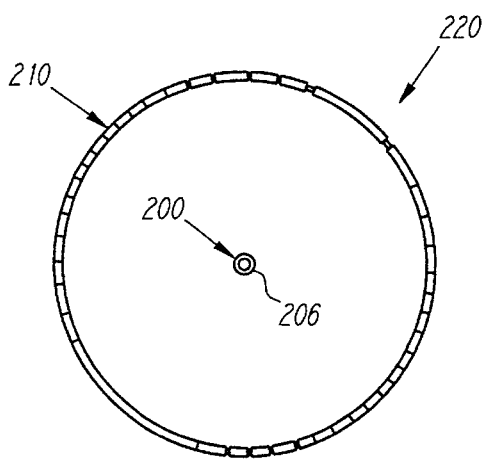
FIG. 4 is a sectional view taken along line 4—4 of FIG. 2.
Figure 5:
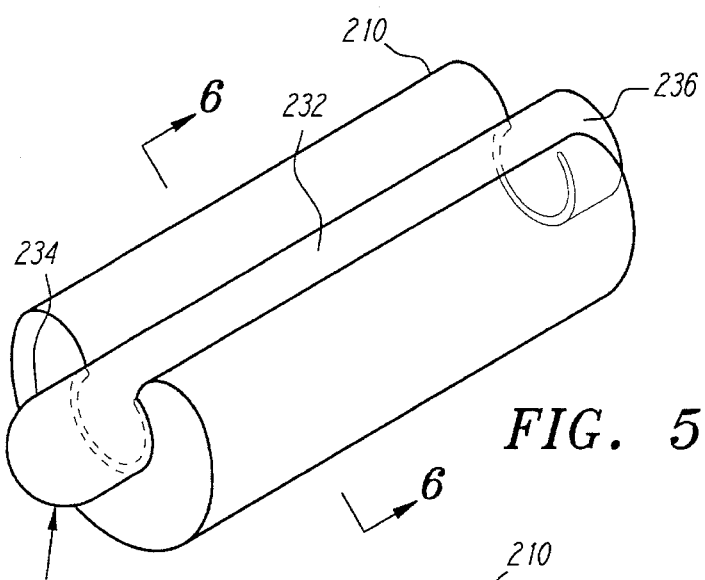
FIG. 5 shows the cannula of FIGS. 1–4 in use with a shape-controlling sleeve.
Figure 6:
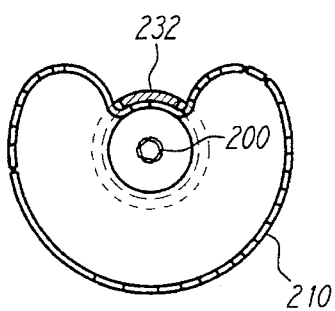
FIG. 6 is a sectional view taken along line 6—6 of FIG. 5.
Figure 7:
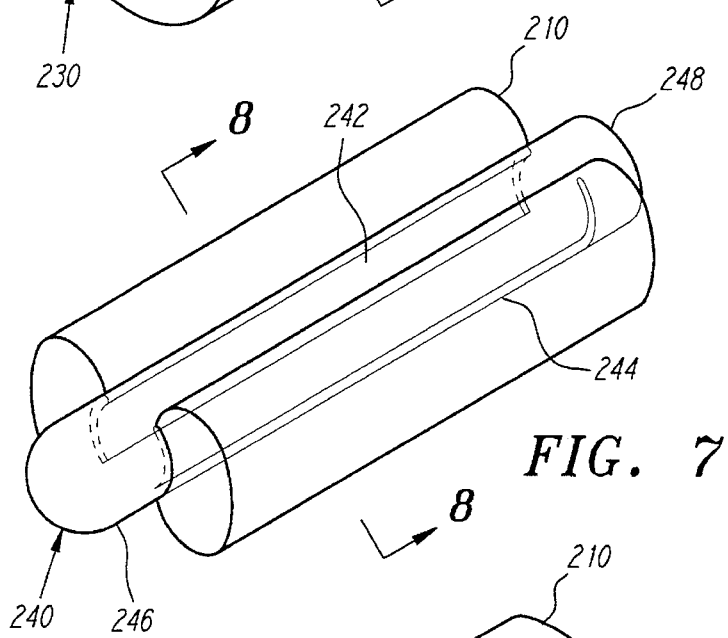
FIG. 7 shows the cannula of FIGS. 1–4 in use with a second shape-controlling sleeve.
Figure 8:
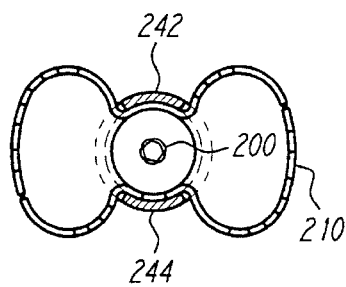
FIG. 8 is a sectional view taken along line 8—8 of FIG. 7.
Figure 9:
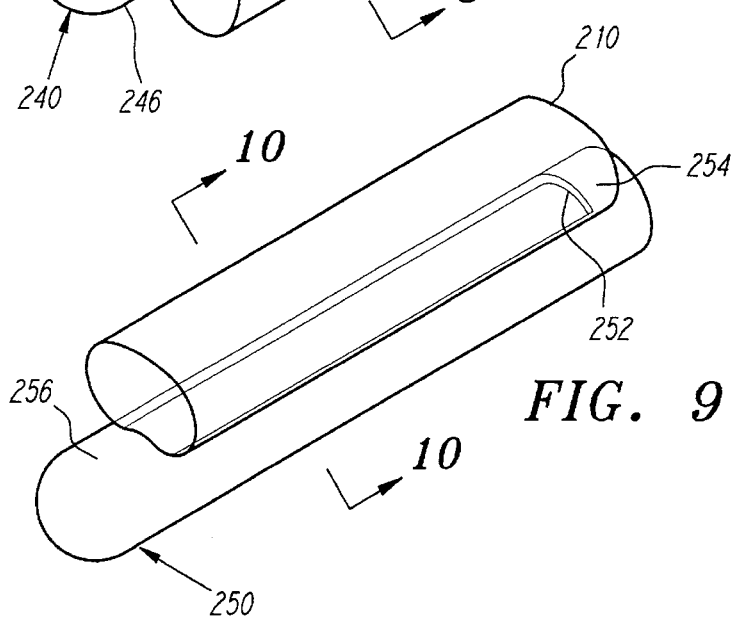
FIG. 9 shows the cannula of FIGS. 1–4 in use with a third shape-controlling sleeve.
Figure 10:
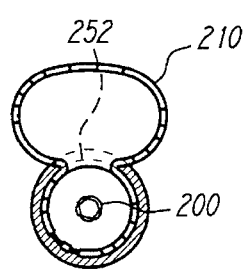
FIG. 10 is a sectional view taken along line 10—10 of FIG. 9.

An embodiment of the invention is illustrated in FIGS. 1–10. A rigid hollow needle 200 has a tubular wall with an inner circumferential surface and an outer circumferential surface. The needle 200 has a pointed tip 202. Proximal to the tip 202 is a radially extending opening 204 which communicates with a central passage 206 defined by the inner circumferential surface of the needle 200. The passage 206 extends to the proximal end 208 of the needle 200.

An elastic balloon 210 is bonded to the needle 200. The balloon 210 is bonded to the needle distally between the tip 202 and a rib 212 adjacent the opening 204. The balloon 210 is also bonded proximally along the needle at 214. The balloon 210 is bonded to the needle 200 so that the balloon 210 does not slide off the needle 210 during insertion and removal. The balloon 210 is preferably made of latex or silicone, or C-Flex® material, a general purpose elastomer sold by Linvatec Corporation of Clearwater, Fla. The balloon 210 is of a small enough diameter such that it is stressed even when fully contracted as seen in FIG. 1. The wall thickness of the balloon 210 is exaggerated in the drawings for clarity.

Together, the needle 200 and the balloon 210 form an expandable cannula 220. The cannula 220 is inserted in tissue (not shown) to the desired location. Then the balloon 210 is inflated by the introduction of fluid under pressure through the passage 206 and the opening 204 into the interior of the balloon 210. The balloon 210 expands radially outwardly to move tissue.

The cannula 220 can be inserted (unexpanded) into the body as an ordinary needle would be used for drawing blood. The balloon 210 is then inflated to expand the surrounding tissues and create a cavity. The viscoelastic nature of the tissue allows the cavity to be maintained when the balloon 210 is rapidly deflated and the cannula 220 is removed. This cavity can then be used as an initial passage for a more conventional cannula or for an expandable cannula, and thus eliminate the need to make an initial incision. The cannula 220 has therefore without cutting tissue made an opening large enough for the passage of surgical instruments.

Alternatively, an insert (not shown) can be slid over the expanded cannula 220. The cannula 220 can then be removed and the insert used as an ordinary cannula.

In one cannula 220 embodiment which has been constructed, the needle 200 is an 18 gauge needle, about 0.042" in diameter. The balloon 210 is about 1.25" long. The balloon 210 when unexpanded on the needle 200 is about 0.060" in diameter, and expands to about 0.315" in diameter. With appropriate material selection, there can be obtained 980% expansion (to failure) of the balloon 210.

One of a series of sleeves can be slid proximally over the cannula 220 prior to expansion to control its expansion. A few examples are illustrated in FIGS. 5–10.

A sleeve 230 (FIGS. 5 and 6) has a single arcuate segment 232 extending between circular end portions 234 and 236. The balloon 210 expands into a kidney shape at all areas between the end portions 234 and 236 other than the area covered by the segment 232. A sleeve 240 (FIGS. 7 and 8) has two arcuate segments 242 and 244 extending between circular end portions 246 and 248. The balloon 210 expands outwardly at all areas between the end portions 246 and 248 other than the areas covered by the segments 242 and 244. A sleeve 250 (FIGS. 9 and 10) has a single arcuate slot 252 extending between circular end portions 254 and 256. The balloon 210 expands outwardly only through the slot 252. Thus, it can be seen that the shape of the balloon 210 can be controlled as it expands.

From the above description of the invention, those skilled in the art will perceive improvements, changes and modifications in the invention. Such improvements, changes and modifications within the skill of the art are intended to be covered by the appended claims.

We claim:

1. An expandable cannula comprising:

a rigid needle member having a tubular wall with an outer circumferential surface and an inner circumferential surface, said needle member having proximal and distal ends, said inner circumferential surface defining in said needle member a longitudinally extending central fluid passage, said needle member having a fluid port extending radially between said outer circumferential surface and said inner circumferential surface and placing the central fluid passage in fluid communication with said outer circumferential surface of said needle member; and a balloon attached to said outer circumferential surface of said needle member, said balloon being bonded to said needle member at at least one location along the length of said needle member;

said cannula having a collapsed condition in which said balloon is contracted on said outer circumferential surface of said needle member, and an expanded condition in which said balloon is expanded radially outwardly from said needle member along substantially its entire length, said cannula further comprising at least one sleeve having at least one expansion slot therein, said sleeve being disposable circumferentially around said balloon, said balloon being expandable radially outwardly against said sleeve and partially through said expansion slot, said sleeve thereby controlling the expansion of said balloon.

2. An expandable cannula as set forth in claim 1 wherein said needle member is about 0.040" in diameter, and said balloon when unexpanded is about 0.060" in diameter, and said balloon expands to about 0.315" in diameter.

3. An expandable cannula as set forth in claim 1 wherein said sleeve has a plurality of expansion slots therein.

* * * * *